United States Patent [19]

Dykstra et al.

[11] 4,410,320

[45] Oct. 18, 1983

[54] WEIGHTED ENTERIC FEEDING TUBE

[75] Inventors: Edward G. Dykstra, East Aurora; Frank P. Wilton, Buffalo, both of N.Y.

[73] Assignee: Ethox Corp., Buffalo, N.Y.

[21] Appl. No.: 297,199

[22] Filed: Aug. 28, 1981

[51] Int. Cl.³ .................................................. A61M 1/00

[52] U.S. Cl. .......................................... 604/27; 604/48

[58] Field of Search ............... 128/348, 349 R, 350 R, 128/DIG. 9, DIG. 16, 276; 604/27, 48, 73, 93, 43, 44, 45, 46, 47, 80

[56] References Cited

U.S. PATENT DOCUMENTS

| | | | |
|---|---|---|---|
| 1,736,182 | 11/1929 | Wilkins | 128/350 R |
| 2,489,067 | 11/1949 | Wild | 128/276 |
| 3,155,097 | 11/1964 | Barron | 128/350 |
| 3,189,031 | 6/1965 | Andersen | 128/350 R |
| 3,794,041 | 2/1974 | Frei et al. | 128/348 |
| 3,885,561 | 5/1975 | Cami | 128/349 R |
| 4,197,840 | 4/1980 | Beck et al. | 128/76 R |
| 4,270,542 | 6/1981 | Plumley | 604/43 |

*Primary Examiner*—Richard J. Apley
*Assistant Examiner*—J. L. Kruter
*Attorney, Agent, or Firm*—Christel, Bean & Linihan

[57] ABSTRACT

An enteric feeding tube including a weighted bolus at its distal end to facilitate insertion and positioning of the tube within the gastrointestinal tract. The tube includes a plurality of spaced apertures adjacent its distal end for the introduction to or extraction from the gastrointestinal tract of fluids or comminuted solids. The weighted bolus includes a plurality of tungsten carbide spheres to provide the necessary weight for proper placement, the spheres being arranged in side-by-side relationship within the tubular bolus, which is so sized as to permit limited axial movement of the spheres to facilitate bending of the bolus as necessary.

8 Claims, 7 Drawing Figures

Fig. 1.
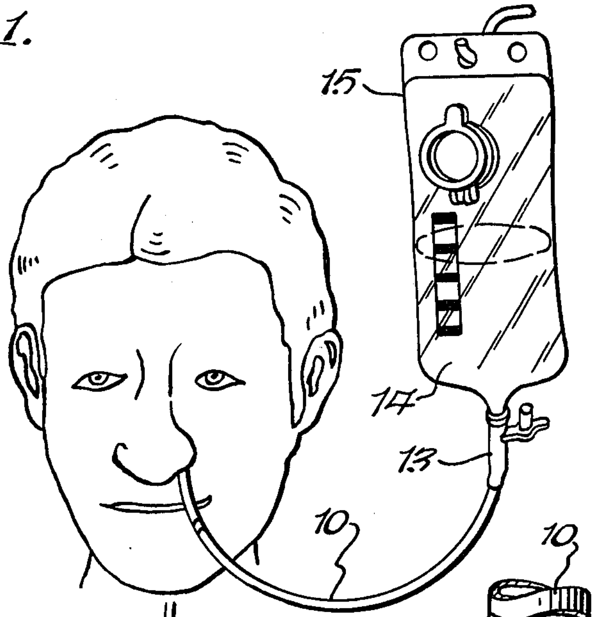
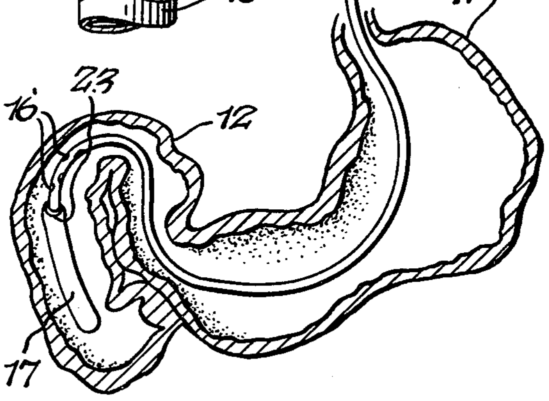
Fig. 2.
Fig. 7.
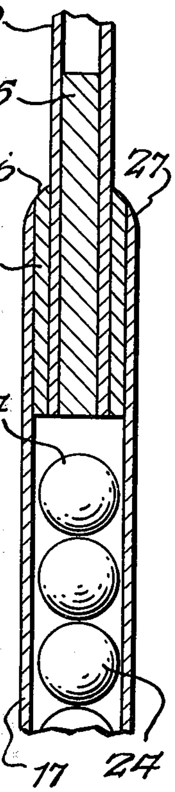
Fig. 4.
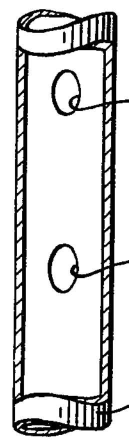
Fig. 3.
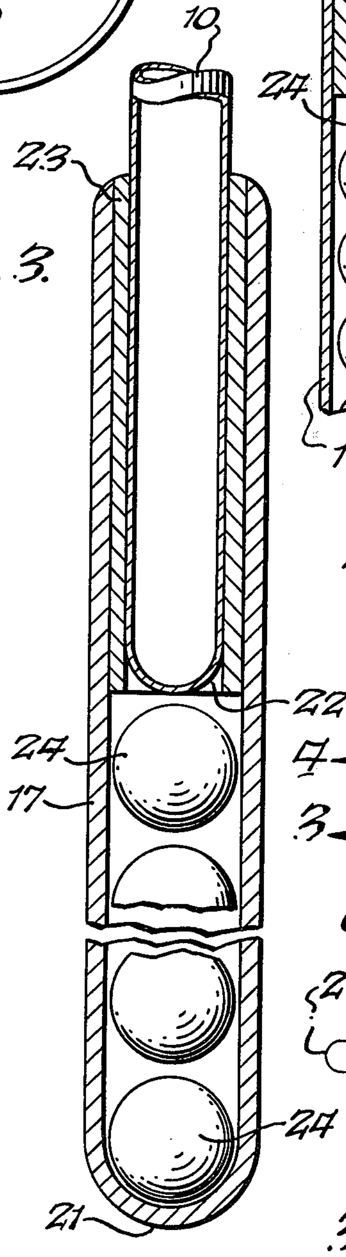
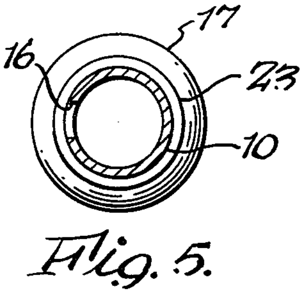
Fig. 5.
Fig. 6.
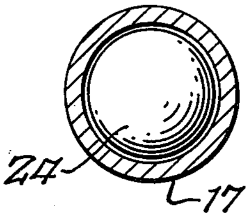

WEIGHTED ENTERIC FEEDING TUBE

BACKGROUND OF THE INVENTION

This invention relates to an enteric feeding tube, and more particularly to an enteric feeding tube having a weighted end and configured to facilitate the insertion, positioning, and retention of such a tube within the gastrointestinal tract.

The necessity to provide nutrition for comatose or otherwise debilitated patients has been addressed in various ways. The technique sometimes utilized has been intravenous feeding wherein the nutrients are directly conveyed into the bloodstream of the patient. Another way in which the problem of restoration and maintenance of fluid and nutritional balance is resolved is by means of intubation, wherein a tube is passed through the nasal passage and into the stomach of a patient, the tube having one or more apertures to permit the introduction of strained or comminuted foods which can be introduced in fluidized form. The intubation approach is often preferred since it permits the introduction of a sufficient number of calories and nutrients to properly utilize the protein, which is also introduced, for the healing of wounds and fractures, for hemoglobin formation, and for the formation of some enzymes and antibodies. When the intravenous approach is utilized it is oftentimes impossible to provide an adequate number of calories for proper utilization of the other nutrients, such as protein.

Among the problems faced in enteric intubation feeding are the insertion of the tube into the body, its proper positioning within the gastrointestinal tract of the patient, and its retention in the desired position. Although it is possible to utilize merely a tube having a plurality of spaced apertures through the side wall thereof, such a tube cannot easily be inserted and positioned within the patient's small intestine, if desired, because of the circuitous path it must traverse through the stomach, the duodenum, and beyond. One approach which has been utilized to permit the proper insertion and placement of the portion of the tube through which the nutrients are passed is the provision of a tube having a weighted end wherein the weighting medium is liquid mercury positioned in a bulb-like structure at the distal end of the tube. Mercury has the advantage of being a material having a relatively high specific gravity, thereby providing considerable weight for a relatively small volume. Additionally, since mercury is a liquid at the temperatures to which it is subjected in such applications, it also has the desirable property of flexibility, which facilitates its passage into and through the gastrointestinal system. However, the use of mercury carries with it several disadvantages, principally involving environmental and safety aspects in connection with the manufacture of such devices and their disposal by hospitals or other users, and also involving possible allergenic reactions. Although liquid mercury itself is not considered by some authorities to be toxic since it is not absorbed in the gastrointestinal tract, the handling of mercury by manufacturers of such tubes generally requires special facilities and handling, which add to the cost of such devices. Additionally, since such devices are normally intended for single use followed by disposal, the disposal of such devices by means of incineration could cause significant health hazards because of the formation upon incineration of mercury vapor, which is considered by some authorities to be toxic because of the fact that it can readily be absorbed. Thus it is desirable to provide a weighting medium which does not involve the handling problems or the disposal problems incident to the use of mercury.

Another prior art approach to weighting the end of an enteric feeding tube, and which does not involve the handling and disposal problem incident to the use of mercury, involves the use of several stainless steel spheres housed within a polyvinylchloride tubular member which has been shrunk over the spheres in such a way that the spheres be maintained in spaced relationship with each other and are incapable of relative movement within the tube. That combination and physical arrangement has been found to provide sufficient weight if the spheres are of a sufficiently large diameter, but its insertion and removal cause patient discomfort because of the sizes of the spheres and tubular member and because of the relatively inflexible tube such an arrangement provides.

It is an object of the present invention to overcome the problems described above and to provide an improved enteric feeding tube in which the desirable end weighting characteristics are retained while at the same time avoiding the handling and disposal problems involved when mercury is the weighting medium.

SUMMARY OF THE INVENTION

Briefly stated, in accordance with one aspect of the present invention, there is provided an enteric feeding tube including a flexible, elongated tubular member adapted for naso-esophogeal insertion into the digestive system. The tube includes a plurality of spaced openings at its distal end to permit the passage of fluid and comminuted solids therethrough. The proximal end of the tube includes means to facilitate the connection of the tube to a source of feeding material or to a mechanism for fluid extraction. The tube includes a weighted bolus at its distal end to facilitate insertion and placement thereof within the body at some predetermined location, the weighted bolus including an elongated, substantially cylindrical inner bore which includes a plurality of metallic weights positioned therein. The weights are positioned in side-by-side longitudinal relationship and the adjacent surfaces of the weights have a rounded shape. The aggregate length of the weights is less than the length of the inner bore in order to permit limited relative axial movement of the weights therewithin. The bulb is secured to the tube in sealing relationship and includes a rounded distal end which is sealed and which facilitates insertion of the weighted end, its movement through the body passages, and its retention in a predetermined position within the body.

BRIEF DESCRIPTION OF THE DRAWING

FIG. 1 is a fragmentary pictorial view, partially in section, showing the use of a weighted enteric feeding tube according to the present invention, including its connection to a source of nutrient material and its positioning at the nasal passage with the distal end thereof positioned in the duodenum.

FIG. 2 is a side view, partially broken away, showing the various portions of the feeding tube according to the present invention.

FIG. 3 is a fragmentary cross-sectional view of the distal end of the feeding tube taken along the line 3—3 of FIG. 2 and showing the construction of the weighted end or bolus.

FIG. 4 is a fragmentary cross-sectional view of a portion of the tube taken along the line 4—4 of FIG. 2.

FIG. 5 is a cross-sectional view of the tube taken along the line 5—5 of FIG. 2.

FIG. 6 is a cross-sectional view through the weighted bolus and taken along the line 6—6 of FIG. 2.

FIG. 7 is a cross-sectional view similar to that of FIG. 3 but showing another embodiment of the invention incorporating a different interconnection and structure at the junction of the tube and the bolus.

DESCRIPTION OF THE PREFERRED EMBODIMENTS

Referring now to the drawing, and particularly to FIG. 1 thereof, there is shown a tube 10 according to the present invention, which extends into one nostril of a patient, through the nasal passage, pharynx, esophagus, and stomach 11, and terminates in the duodenum 12. Tube 10 extends outside the patient's body to a proximal end which includes a fitting 13 adapted to be connected to a source of nutrients 14. The nutrients can be provided as a liquid or as a slurry involving a solution of comminuted solids, and can be carried in a container 15 supported at a higher elevation than the patient to insure downward flow into tube 10 and then into the patient's body. Tube 10 includes a plurality of apertures 16 adjacent its distal end through which the nutrients pass to enter the patient's gastrointestinal tract. A weighted end or bolus 17 is provided to facilitate insertion of tube 10 and ultimate placement of apertures 16 in the desired position within the gastrointestinal tract. Bolus 17 also facilitates the retention of tube 10 in the desired position.

Although shown as positioned with apertures 16 in the duodenum, tube 10 could be so positioned that apertures 16 are either within the stomach itself, within the duodenum, or within the jejunum. Determination of the position of the tube and its apertured section can be accomplished radiographically by incorporating in the tube material a radiopaque substance, such as, for example, bismuth, or a barium compound such as barium sulfate.

Tube 10 can be formed from any of a number of materials, but it is desired that the material be such as to be sufficiently flexible for the tube to be comfortably inserted and removed, and also that it be capable of passing through the circuitous passageways within the body without excessive discomfort to the patient. At the same time, it is desired that tube 10 be sufficiently rigid that it does not roll over upon itself or kink upon insertion or during the course of passage through the body to the desired location, to thereby obstruct the flow of materials therethrough. Although it is possible to form the tube from a flexible material such as polyvinyl chloride, that particular material has a drawback in that prolonged use could result in the leaching out of the plasticizers by the action of the gastric environment, thereby rendering the tube less flexible and possibly increasing the patient's discomfort during removal of the tube from within the patient's body. A preferred tube material which contains no plasticizers is polyurethane, which has been found to provide the desired flexibility and strength characteristics, and most preferably an extrusion-grade, polyether-type polyurethane designated PE-90, and manufactured by K. J. Quinn & Company, Inc., 195 Canal Street, Walden, Mass. 02148.

The various components comprising tube 10 are best seen in FIG. 2, which shows a portion of tube 10, which can be of the order of four feet or so in length for adults. For pediatric use the tube can be of the order of 33 inches. At the upper, or proximal, end of tube 10 there is positioned fitting 13 which includes an opening into which an integrally formed closure 18 can be inserted to seal the tube at the times when feeding is not taking place. Fitting 13 can be adapted for use either with male luer taper syringes or standard needle adaptors. At its distal end, tube 10 includes a plurality of spaced apertures 16, the apertures preferably being spaced axially along the tube and alternating around the periphery thereof at approximately 180° intervals as shown in FIGS. 1 and 2. For a tube which is designated as a size 8 French, which would be suitable for use in adults, the outer diameter is about 0.105 inches and the internal diameter is about 0.071 inches, and for a tube of that size the preferred size of the apertures is about 0.109 inches in length and about 0.043 inches in width and of a configuration as best seen in FIG. 4. In the embodiment shown the apertures are axially spaced approximately 0.28 inches apart, although the aperture sizes, shapes, and spacings can be varied, as desired. Furthermore, tubes varying from 3.5 French (outer diameter of 0.045 inches) to 18 French (outer diameter of 0.236 inches) can be utilized, the smaller sizes being intended principally for pediatric use, and the larger sizes most often for use with adults.

Tube 10 includes depth indicators which can be positioned at various predetermined points along the length thererof. For example, a single circumferential mark 19 can be applied at the 24 inch point, and a double circumferential mark 20 can be provided at the 32 inch mark, in order to provide an approximate indication of the position of the distal end of the tube within the adult patient's body. As will be appreciated, different spacings are normally provided for pediatric use.

Secured to the distal end of tube 10 is a weighted end or bolus 17 which is preferably of tubular cross-section and which terminates in a rounded, closed end 21. As shown in phantom in FIG. 2, bolus 17 is also flexible and is capable of bending to facilitate insertion and passage through the body. Preferably, bolus 17 is also formed from polyether-type polyurethane, and for a size 8 French tube a bolus having an inner diameter of about 0.133 inch and a wall thickness of about 0.020 inch has been found to be satisfactory.

As shown in FIG. 3, tube 10 is closed at its distal end 22 to prevent entry of nutrients and other materials into bolus 17. A sleeve 23 is provided between the distal end of tube 10 and the open end of bolus 17, the sleeve having an inner diameter corresponding approximately with the outer diameter of tube 10 and an outer diameter corresponding approximately with the inner diameter of bolus 17 to provide a snug fit therebetween (see FIG. 5). Sleeve 23 can be formed of polyether urethane and can be solvent sealed both to tube 10 and to bolus 17 by means of cyclohexanone or another solvent effective with polyurethane. Preferably, the proximal ends of bolus 17 and of sleeve 23 are rounded to minimize discomfort during withdrawal of the tube from the patient's body.

The interposition of sleeve 23 between tube 10 and bolus 17 serves as a transition member between those two elements of the feeding tube, both of which have dissimilar outer diameters and dissimilar wall thicknesses. If desired, sleeve 23 can be positioned so that it extends beyond the proximal end of bolus 17 and along the outer surface of tube 10, in which case it operates to reduce the tendency of right angle or greater bending of tube 10 with respect to bolus 17 and thereby minimizes collapse or kinking of tube 10 adjacent the proximal end of bolus 17, which could impede proper positioning of bolus 17 within the body, or could otherwise obstruct the flow of materials through apertures 16.

As an alternative construction, the distal end of tube 10 can be left open and an elongated cylindrical plug 25 inserted therein, as shown in FIG. 7, and secured thereto, as by solvent sealing. Plug 25 serves to provide support for the small diameter, relatively thin wall of tube 10 at the point of its attachment to the larger diameter and relatively thicker wall of bolus 17, and it also serves to close the distal end of tube 10 and thereby eliminates the need for forming the rounded end 22 shown in FIG. 3. As in the embodiment of FIGS. 2 and 3, a sleeve 23 can be provided for a tighter fit of the distal end of tube 10 to the open end of bolus 17. As shown, the outwardly extending edge 26 of sleeve 23 and the open end 27 of bolus 17 are preferably rounded to minimize patient discomfort upon withdrawal of the tube from the patient's body. Preferably, plug 25 extends into tube 10 beyond the open end 27 of bolus 17 and is intended to reduce the tendency of foldover or right angle or greater bending at the juncture of tube 10 and bolus 17, which could impede the proper positioning of bolus 17 within the patient's body.

Positioned within bolus 17 is a weighting medium, which, as shown, comprises a plurality of weights 24 in the form of spheres. Although shown as having a spherical configuration, weights 24 can be of any desired shape but preferably have rounded ends so that when bolus 17 is flexed or bent, weights 24 do not impede such flexing or bendng. For example, weights 24 can be of cylindrical cross-section with rounded ends, if desired.

The preferred material for the weighting medium is a relatively heavy material, preferably one having a specific gravity greater than that of mercury so that a bolus having an equivalent or smaller outer diameter will be of sufficient weight to satisfy the requirements for insertion, positioning, and retention. It has been found that tungsten carbide, which has a specific gravity of from about 14.85 to about 15.05 (as compared with the specific gravity of mercury, which is 13.55), permits the construction of a suitable weighted end without the necessity for a bolus of excessive diameter or length to provide the necessary weight. Although disclosed in terms of tungsten carbide, other materials having a specific gravity greater than 13.55, including substantially pure tungsten, can also be used.

As shown in FIGS. 2, 3, and 7, the tungsten carbide spheres are positioned side-by-side within bolus 17 and preferably have a diameter which is slightly smaller than the internal diameter of bolus 17 in order to permit the weights to move freely in an axial direction within bolus 17 for a limited distance, and thereby permit bolus 17 to flex in a transverse direction as necessary during insertion and removal. The amount of axial movement of the weights depends upon the relative spacing between closed end 21 of bolus 17 and the distal end of tube 10. The weights are of such a number relative to the axial length of bolus 17 as to substantially completely fill the interior length of bolus 17 yet permit some limited axial movement. Preferably the axial movement permitted is a distance less than the axial length of one weight 24. If additional axial space beyond that is permitted, there is a risk of possible folding over or kinking of bolus 17 as it passes through the body and bends to pass around abrupt corners.

In an embodiment of the invention wherein an 8 French polyether urethane tube is employed, suitable for use in adults, a polyurethane bolus is provided having an overall length of about 2.56 inches, an inner diameter of 0.133 inches and a wall thickness of 0.020 inches. The tungsten carbide spheres which can be utilized in such a bolus preferably have a diameter of 0.125 inches and 16 such spheres can be employed. In the embodiment shown in FIGS. 2 and 3 a suitable sleeve can have a length of 0.75 inches, an outer diameter of 0.130 inches and an inner diameter of 0.100 inches. In the embodiment of FIG. 7 the sleeve can have a length of 0.50 inches, the plug a length of 0.75 inches and a diameter of 0.07 inches, and the plug can extend within tube 10 and beyond open end 26 of bolus 17 a distance of about 0.25 inches.

In operation, bolus 17 is slowly and gently passed into and through the patient's nostril, preferably while the patient is in at least a semi-upright position, whereupon the weighted end carries the tube through the nasal passage. Thereafter the bolus enters the pharynx and the patient is encouraged to swallow continuously to cause the bolus to enter the esophagus and not the trachea. The swallowing action will carry the bolus into the stomach and it can be left in that position, if desired, for direct stomach feeding. When the bolus is in the stomach, the single line on the outer surface of the tube will be approximately at th entrance to the nostril. Alternatively, the bolus can be permitted over a period of several hours to pass through the stomach and into the duodenum or into the jejunum, at which point the double line on the outer surface of the tube will be approximately at the entrance to the nostril. A more accurate determination of the position of the bolus, and the tube itself, can be obtained by X-ray or by fluoroscopic examination, provided the tube has been rendered radiopaque through the addition of bismuth or a barium compound, such as barium sulfate, to the material from which the tube is formed. The weights within the bolus are radiopaque, and thus the bolus itself need not include bismuth or barium compounds.

If the bolus and tube are not radiopaque, or if X-ray or fluoroscope equipment are not to be used, the position of the tube, and therefore of the apertures, can be determined by injection with a syringe of small quantities of air (approximately 5–10 cc.) into the tube and listening over the patient's stomach with a stethoscope. If the tube is positioned within the apertures in the stomach, the air will be heard as a bubbling sound; if the tube is coiled with the apertures in the esophagus, the patient will belch. Another way to check for proper positioning of the apertures in the stomach is to use a syringe to exract a specimen of fluid and verify by appearance and order that it is gastric fluid.

Although shown and described in terms of its function as an enteric feeding tube, it will be apparent that the tube of the present invention can also be utilized for purposes of extracting gastric fluids for purposes of examination and analysis, and for the direct internal administration of medications, if desired, While particular embodiments of the invention have been illustrated and described, it will be apparent to those skilled in the art that various changes and modifications can be made, and it is intended to cover in the appended claims all such changes and modifications that fall within the scope of the present invention.

What is claimed is:

1. In an enteric feeding tube including a flexible, elongated tubular member adapted for nasogastric and nasointestinal use, said tube having a weighted bolus at its distal end to facilitate the placement of said tube within the body and having a longitudinal axis, and a plurality of spaced openings in the wall of said tube adjacent the distal end thereof to permit the passage of fluids and comminuted solids to and from said tube, the proximal end thereof including means to facilitate the connection of said tube to a fluid feeding or fluid extraction arrangement, the improvement comprising said weighted bolus having an elongated, substantially cylindrical inner bore, a plurality of metallic weight means of a diameter substantially equal to and slightly smaller than said inner bore singularly positioned in side-by-side relationship within and extending longitudinally along said inner bore of said bolus, said weight means having adjacent surfaces of rounded shape and having an aggregate length less than the length of said inner bore to permit limited movement of said weight means relative to and along the longitudinal axis of said bore and to permit said bolus to bend as necessary, said bolus having a rounded distal end to facilitate movement through the body passages and secured at its proximal end to said tube in sealing relationship.

2. The feeding tube of claim 1 wherein the length of the inner bore of said bolus is greater than the aggregate length of said weight means placed end-to-end by less than the axial length of one of said weight means.

3. The feeding tube of claim 2 wherein the diameter of said inner bore is slightly greater than the diameters of said weight means, whereby to permit relatively free axial movement of said weight means within said bolus and provide increased flexibility to said bolus.

4. The feeding tube of claim 3 wherein said weight means have a specific gravity greater than 13.55.

5. The feeding tube of claim 4 wherein the inner diameter of said bolus is greater than the outer diameter of said tube and said tube includes an intermediate cylindrical outer sleeve positioned at the distal end thereof, said sleeve overlying a portion of the end of said tube and positioned within the proximal end of said bolus.

6. The feeding tube of claim 5 wherein said weight means are spherical.

7. The feeding tube of claim 5 wherein a portion of said sleeve extends beyond the proximal end of said bolus, whereby to provide a gradual transition between said tube and said bolus to minimize kinking of said tube adjacent said bolus.

8. The sealing tube of claim 5, wherein said tube is closed at its distal end.

* * * * *